United States Patent [19]
Stoller

[11] Patent Number: 6,086,923
[45] Date of Patent: *Jul. 11, 2000

[54] METHOD FOR INHIBITING PLANT DISEASE

[75] Inventor: Jerry Herman Stoller, Houston, Tex.

[73] Assignee: Stoller Enterprises, Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/828,995

[22] Filed: Mar. 31, 1997

Related U.S. Application Data

[63] Continuation of application No. 08/330,367, Oct. 27, 1994, abandoned.

[51] Int. Cl.$^7$ .......................... A01N 59/00; A01N 59/06; A01N 59/08; A01N 59/16; A01N 59/20; C05C 9/00; C05G 3/08

[52] U.S. Cl. .......................... 424/678; 424/632; 424/633; 424/634; 424/635; 424/637; 424/639; 424/640; 424/641; 424/646; 424/647; 424/675; 424/681; 424/682; 424/686; 424/688; 424/692; 424/693; 424/718; 424/722; 424/630; 514/492; 514/494; 514/499; 514/501; 514/502; 514/588; 71/31; 504/101; 504/187; 504/188

[58] Field of Search .................................. 504/101, 187, 504/188; 514/588, 492, 494, 499, 501, 502; 424/678, 630, 632–635, 637, 639–641, 646–647, 675, 681–682, 686, 688, 692, 693, 718, 722; 71/31

[56] References Cited

U.S. PATENT DOCUMENTS 4,500,335  2/1985  Fenn .......................................... 71/28

FOREIGN PATENT DOCUMENTS

| 57-131708 | 8/1982 | Japan . |
|---|---|---|
| 1583482 | 8/1990 | Russian Federation . |
| 1734622 | 5/1992 | Russian Federation . |
| 1561136 | 2/1980 | United Kingdom . |
| WO 90/11262 | 3/1990 | WIPO . |
| WO93/22911 | 3/1993 | WIPO . |

OTHER PUBLICATIONS

Abstract No. 123: 105060F; *Chemical Abstracts;* vol. 123; p. 384 (1995).

Bicici, M., et al.; Cultural, Chemical, Physical and Biological Methods to Control Stem Rot, Sclerotium Rolfii Sacc., in Peanut; Turkish J. of Agriculture and Forestry; vol. 18; pp. 423–435 (1994).

Lockwood, J.L.; Approaches to Biological Control of Soybean Root Diseases; Plant Prot. Bull. (Taiwan, R.O.C.); vol. 27; pp. 279–293 (1985).

Elad, Y., et al.; Calcium Reduces Botrytis Cinerea Damages to Ruscus Hypoglossum; *Phytoparasitica;* vol. 20, pp. 285–291, (1992).

Power, R.H.; Relationship Between the Soil Environment and Tomato Resistance to Bacterial Wilt (Pseudomonas Solanacearum) *Surinaamse Landbouw;* vol. 31, pp. 39–47 (1983).

Biggs et al., "Control of Alternaria Infection of Fruit of Apple Cultivar Nittany with Calcium Chloride and fungicides", Plant Disease, vol. 77 (10), pp. 976–980.

CABA Abstract 83:70918 (1982), abstracting: Javed, "Field efficacy of reduced rates of various 50% Copper fomulations against coffee berry disease in Kenya," Kenya Coffee, vol. 47 (560), 1982, pp. 273–280.

*Primary Examiner*—John Pak
*Attorney, Agent, or Firm*—Shook, Hardy & Bacon, L.L.P.

[57] ABSTRACT

The present invention is directed to a method of inhibiting the growth of disease organisms on and in plants by directly applying an aqueous solution comprising urea and at least one water-soluble salt of a divalent cation and a monovalent anion to the seeds, stems, bark, leaves, seed heads or sub-surface root zones of said plants. The weight percent ratio of urea to divalent cation in these solutions should be from about 0.25–10.0 to 1.0. Preferred divalent cations include those of the alkaline earth metals and the transition metals. Most preferred are calcium, magnesium, zinc, manganese, copper, iron, cobalt, nickel and mixtures thereof. Preferred anions include nitrate, chloride, bromide and mixtures thereof. In more preferred solutions, the ratio of urea to divalent cation is from about 2.0–7.0 to 1.0. Particularly preferred solutions include calcium chloride as the water-soluble salt. Optionally, a second water-soluble salt of a divalent cation and a monovalent anion may be included.

16 Claims, No Drawings

METHOD FOR INHIBITING PLANT DISEASE

This is a continuation of U.S. patent application Ser. No. 08/330,367 filed on Oct. 27, 1994, and now abandoned.

BACKGROUND OF THE INVENTION

1. Field of the Invention

The present invention generally relates to a method for inhibiting a variety of diseases in plants. More specifically, the present invention is directed to methods for inhibiting diseases in plants by applying an aqueous solution of urea and at least one water-soluble salt of a divalent cation and a monovalent anion to the seeds, stems, leaves, seed heads or sub-surface root zone soil of said plants.

2. Description of the Background

A variety of metal-containing solutions have been used over the years to control bacterial and fungal disease in plants. Examples of metallic compounds used in these solutions include tribasic copper sulfate, copper oxychloride, copper hydroxide, Bordeaux solutions and the bis dithiocarbomates of zinc, iron and manganese. These metallic compounds are substantially insoluble in water and protect the crops from the outside surface of the plant leaves and stems where they inhibit growth of various bacteria and fungi. If these compounds were water soluble, they would be toxic to plant tissue in the concentrations in which they are applied.

Water soluble compounds, including calcium nitrate, calcium chloride and calcium sulfate, have been reported to control soft rot on potatoes and club root on brassica crops when applied to the surface of surrounding soil. The inventor is unaware of any compound of magnesium which has been reported to provide any fungal or bacterial control.

In summary, it is known that soluble calcium compounds may be used to control soil borne diseases when soil applied while several non-soluble metallic compounds have been reported to control foliar diseases when applied to the surfaces of leaves and stems of plants.

While urea has not been used to control plant disease, urea, being approximately 46 percent-by-weight nitrogen, has long been preferred as a nitrogen source for fertilizing soils to stimulate plant growth. However, high ammonia losses when used in the presence of moisture effectively restricted use of urea for many years. It is believed that these losses are caused by the hydrolysis of urea, in the presence of moisture and the enzyme urease, according to the following reaction:

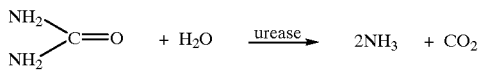

However, when urea is mixed in a solution with a water-soluble salt comprising a divalent alkaline earth metal or a divalent transition metal and a monovalent anion, the urease activity illustrated in the above equation is inhibited. In order to inhibit this urease activity, it has been found that the soluble salt must comprise a divalent cation, together with a monovalent anion. Exemplary inhibiting salts are the chlorides and nitrates of calcium, magnesium, manganese and zinc. The inventor believes that these salts inhibit urease activity according to the following reaction:

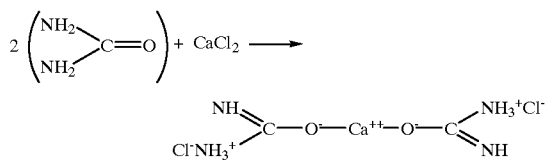

Aqueous solutions of urea and the described soluble salts have been proposed for use as fertilizers. See the proposal in British Patent No. 1,561,136 which, while directed to the use of these solutions as liquid nutrient supplements for animal feeds, suggests their use for plant fertilization. Also, see U.S. Pat. No. 4,500,335 which proposes the application of urea in the presence of salts of calcium or magnesium as a method for reducing ammonia volatilization from surface applied urea-containing fertilizers.

However, no known references have suggested that these solutions be directly applied to plants for the purpose of inhibiting various fungal and bacterial diseases. Accordingly, while similar solutions have been generally known, the agricultural industry has continued to employ a variety of toxic chemicals, including those mentioned in the first paragraph above, to control fungal and bacterial diseases in plants. There has been a long felt but unfulfilled need in the industry for an effective, but non-toxic, method of inhibiting growth of fungal and bacterial diseases in a variety of crop plants. The present invention solves that need.

SUMMARY OF THE INVENTION

The present invention is directed to a method for inhibiting the growth of disease organisms on and in plants by directly applying an aqueous solution comprising urea and at least one water-soluble salt of a divalent cation and a monovalent anion to the seeds, stems, bark, leaves, seed heads or sub-surface root zones of the plants. These inhibiting solutions should be applied at the rate of about 2–100 gallons per acre. While application temperatures are restricted by the freezing and boiling points of the solutions, it is preferred that these solutions be applied at ambient temperatures between about 35° F. and 100° F., preferably between about 50° F. and 80° F.

The inhibiting solutions may comprise up to about 40 percent-by-weight urea. Preferably they comprise about 1 to 40 percent-by-weight urea, most preferably about 15 to 40 percent-by-weight urea. The weight percent ratio of urea to divalent cation should be from about 1 to 4 to about 10 to 1, while the preferred ratio is from about 2 to 1 to about 7 to 1.

Any divalent metal may be used. However, the divalent cation preferably is selected from the alkaline earth metals and the transition metals. Preferred cations include calcium, magnesium, zinc, manganese, copper, iron, cobalt, nickel and mixtures thereof. Any non-toxic monovalent anion may be used. Preferred monovalent anions include nitrate, chloride, bromide and mixtures thereof. The preferred water-soluble salts include the nitrates and chlorides of calcium, magnesium, zinc, manganese and copper. Calcium chloride is the presently most preferrable water-soluble salt. While the solution need contain only a single such water-soluble salt, it has been found that solutions containing two such salts, one having a divalent alkaline earth cation, the other having a divalent transition metal cation and both with monovalent anions, are particularly preferred.

The method of the present invention is applicable to inhibit the growth of a variety of disease organisms, including those causing fire blight, black leg, neck rot, blight, soft rot, club root, rizocotina, botritus and head smut. Crop plants effectively treated by the method of the present invention include a variety of tree, crucifer, tuber, and seed bearing crops. Excellent results have been observed with the following exemplary crops: apples, pears, potatoes, onions, radishes, cauliflowers, strawberries and wheat. The foregoing diseases and crops, are not meant to be exclusive, but merely are exemplary of the benefits achievable with the method of the present invention.

In the method of the present invention, the aqueous solution of urea and water-soluble salt should be applied directly to the plant material. For example, solutions should be applied to the bark and stems of apples, pears and other fruit trees during the spring before leaves appear. The inhibiting solutions may be applied directly to the seed of crucifer crops, e.g., radishes, cauliflower, mustard and the like. Tubers and similar crops may be treated by direct application to the sub-surface soil in the root zone of the plant. Wheat is conveniently treated by direct application to the seed head during the grain filling period.

The present invention provides a method of inhibiting a variety of fungal and bacterial diseases in many crop plants by directly applying an aqueous solution of urea and a water-soluble salt of a divalent metal cation and a monovalent anion to the plant surfaces of the crops. These inhibiting solutions provide both fertilization in plant growth and inhibition of the growth of many bacterial and fungal diseases. These and other meritorious features and advantages of the present invention will be more fully appreciated from the following detailed description and claims.

DETAILED DESCRIPTION OF THE PREFERRED EMBODIMENT

The present invention provides a method of inhibiting a variety of fungal and bacterial diseases in many crop plants by directly applying an aqueous solution of urea and at least one water-soluble salt of a divalent metal cation and a monovalent anion to the plant surfaces of the crops. These solutions provide both nutrients to improve plant growth and inhibitors to retard or prevent growth of a variety of fungal and bacterial diseases.

The inventor has discovered that the ability of urea to suppress disease is markedly improved when combined in an aqueous solution with one or more water-soluble salts of a divalent cation and a monovalent anion. In particular, it has been discovered that these solutions suppress disease when applied to the seeds, leaves, stems, bark or seed heads of plants or to the sub-surface soil in the root zones of the plants. Solutions where the water-soluble salt comprises the chloride or nitrate of calcium are particularly preferred. Where these solutions further contain the chloride or nitrate of copper or zinc, they have been found to suppress an even wider spectrum of diseases.

It is believed that these solutions are directly toxic to disease organisms upon contact. In addition, because the salts and urea are water soluble, they may be absorbed into the plants where they remain toxic to disease organisms which may later invade the plants. Application of these solutions has been found to raise the measured level of the applied cation in the plant tissue. It is believed that these higher levels of divalent cation inhibit growth of bacterial and fungal disease organisms in the plant.

It is known that most plants experience normal growth when copper levels in the plant tissue are maintained in the range of about 6–14 ppm. Similarly, normal growth is achieved when zinc levels are maintained in the range of about 20–40 ppm. However, when the level of these trace metals is increased about 2–4 times, it has been found that disease organisms cannot colonize on or in the plants. While these organisms cannot tolerate these higher levels of metallic ions, such levels are acceptable to the plants. In general, raising the levels of divalent alkaline earth metal cations and divalent transition metal cations in the tissue of plants to a level that is about 2 to 4 times the normal level prior to being treated with the aqueous solution of the invention has been found to inhibit the growth of disease organisms on and in plants. It also is believed that many disease organisms affect host plants by excreting plant toxins such as oxalic acid. Soluble calcium absorbed within the plant may neutralize such toxins. Levels of calcium about 2–3 times normal have been found to accomplish this goal.

The present invention is directed to a method for inhibiting the growth of disease organisms on and in plants by directly applying an aqueous solution comprising urea and at least one water-soluble salt of a divalent cation and a monovalent anion to the seeds, stems, bark, leaves, seed heads or sub-surface root zones of the plants. These solutions should be applied at the rate of about 2–100 gallons per acre. While application temperatures are restricted by the freezing and boiling points of these solutions, it is preferred that these solutions be applied at ambient temperatures between about 35° F. and 100° F., more preferrably between about 50° F. and 80° F.

These solutions may comprise up to about 40 percent-by-weight urea. Preferrably, they comprise about 1 to 40 percent-by-weight urea, most preferrably about 15 to 40 percent-by-weight urea. The weight percent ratio of urea to divalent cation should be from about 1 to 4 to about 10 to 1, while the preferred ratio is from about 2 to 1 to about 7 to 1.

While any divalent metal cation may be used, the divalent cation preferrably is selected from the alkaline earth metals and the transition metals. Preferred cations include calcium, magnesium, zinc, manganese, copper, iron, cobalt, nickel and mixtures thereof. The anion must be monovalent. Preferred monovalent anions include nitrate, chloride, bromide and mixtures thereof. The presently preferred water-soluble salts include the nitrates and chlorides of calcium, magnesium, zinc, manganese and copper. Calcium chloride is the presently most preferred water-soluble salt. It is believed that these salts form complexes with urea having the formula:

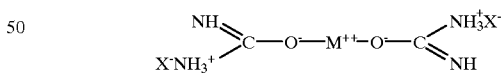

where $M^{++}$ is a divalent metal cation and $X^-$ is a monovalent anion. While the solution need contain only a single such water-soluble salt, it has been found that solutions containing two such salts, one having a divalent alkaline earth cation, the other having a divalent transition metal cation, both with monovalent anions, are particularly preferred.

The method of the present invention is applicable to inhibit the growth of a variety of disease organisms, including those causing fire blight, black leg, neck rot, blight, soft rot, club root, rizocotina, botritus and head smut. Crop plants effectively treated by the method of the present invention include a variety of tree, crucifer, tuber and seed bearing crops. Exemplary crops are apples, potatoes, onions, radishes, cauliflowers, strawberries and wheat. The foregoing diseases and crops are not meant to be exclusive, but merely are exemplary, of the benefits achievable with the method of the present invention.

In the method of the present invention, the aqueous solutions of urea and water-soluble salt should be applied directly to the plant material. For example, the solutions should be applied to the bark and stems of apples, pears and other fruit trees during the spring before leaves appear. The solutions may be applied directly to the seed of crucifer crops, e.g., radishes, cauliflower, mustard and the like. Tubers and similar crops may be treated by direct application of the solutions to the sub-surface soil in the root zone of the plants. Wheat is conveniently treated by direct application of the solutions to the seed head during the grain filling period.

The present invention will be more fully understood with the following specific examples.

Table I illustrates several solutions useful in the method of the present invention.

TABLE I

| Analysis | Ingredients | Percent-by-weight | % Urea % Divalent Cation |
|---|---|---|---|
| 18-0-0-7(Ca) | Water | 35.9 | 5.6:1 |
|  | Urea (46% N) | 39.1 |  |
|  | Calcium Chloride (28% Ca) | 25.0 | 5.6:1 |
| 18-0-0-7(Ca) | Water | 24.5 |  |
|  | Urea | 39.1 |  |
|  | Calcium Nitrate (19% Ca) | 36.8 |  |
| 9-0-0-9(Ca) | Water | 48.3 | 2.2:1 |
|  | Urea | 19.6 |  |
|  | Calcium Chloride (28% Ca) | 32.1 |  |
| 18-0-05(Ca)-1.5(Mg) | Water | 21.6 | 6.0:1 |
|  | Urea | 39.1 |  |
|  | Calcium Chloride (28% Ca) | 17.9 |  |
|  | Magnesium Chloride (7% Mg) | 21.4 |  |
| 9-0-0-7(Ca)-1.5(Cu) | Water | 51.7 | 2.3:1 |
|  | Urea | 19.6 |  |
|  | Calcium Chloride (28% Ca) | 25.0 |  |
|  | Copper Chloride (41% Cu) | 3.7 |  |

Fire blight on apple and pear trees has been successfully inhibited by application of a solution containing urea and divalent metal cation in the ratio of about 2.3 to 1 and having the following formula:

9.0% Nitrogen (19.6% Urea)
7.0% Calcium from Calcium Chloride
1.5% Magnesium from Magnesium Chloride
0.01 % Copper from Copper Chloride
Balance Water The foregoing solution was sprayed on apple and pear trees at the rate of about 20–30 gallons per acre in the spring prior to leaf formation using a regular orchard sprayer. A reduction in fire blight of about 50% in comparison to untreated trees was observed.

Club root on crucifer crops was reduced by application of an aqueous solution containing urea and divalent cation in the ratio of about 2.3 to 1 and having the following formula:

9.0% Nitrogen (19.6% Urea)
7.0% Calcium from Calcium Chloride
1.5% Magnesium from Magnesium Chloride
Balance Water An aqueous solution having the foregoing composition was applied at the rate of about 6–10 gallons per acre directly onto the seed, i.e., into the seed furrow, while planting crucifer seeds, e.g., radish, mustard and cauliflower. Reductions of club root in the range of about 80% in comparison to untreated crops were observed.

Soft rot on potatoes was inhibited by application of an aqueous solution containing urea and divalent metal cation in the ratio of about 2.2 to 1 and having the following formula:

9.0% Nitrogen (19.6% Urea)
9.0% Calcium from Calcium Chloride
Balance Water

The foregoing aqueous solution was applied to the sub-surface soil in front of a cover disc at the rate of about 20–100 gallons per acre. About 80% reduction of soft rot was observed.

Head smut on wheat has been reduced by application of an aqueous solution containing urea and a divalent metal cation in the ratio of about 4.1 to 1 and having the following formula:

15% Nitrogen (19.6% Urea)
7% Calcium from Calcium Chloride
1% Magnesium from Magnesium Chloride
Balance Water The foregoing aqueous solution was applied at the rate of about 2–10 gallons per acre directly onto the seed head of the wheat during the grain filling period. About 90% reduction of head smut was observed.

Rhizoctonia on sugar beets was inhibited by application of an aqueous solution containing urea and divalent metal cation in the ratio of about 3.3 to 1 and having the following formula:

12% Nitrogen (19.6% Urea)
8% Calcium from Calcium Chloride
Balance Water

The foregoing aqueous solution was applied at the rate of about 5–25 gallons per acre into the sub-surface soil in an eight inch band directly over the row during planting. About 60% reduction of rhizoctonia was observed.

Other examples of similar treatment of various crops with solutions and methods in accord with the present invention are illustrated in Table II.

TABLE II

| Analysis* | % Urea % Divalent Cation | Application Rate (gal/acre) | Crop Treated | Application Method | Disease Organism | Results (% control) |
|---|---|---|---|---|---|---|
| 9-0-0-7.5 Ca-1.5 Mg. | 2.2:1 | 25 | Apple | Sprayed on tree bark | Fire Blight | 50 |
| 9-0-0-9-1.5 Cu | 1.9:1 | 30 | Apple | Sprayed on tree bark | Fire Blight | 90 |
| 9-0-0-9 Ca | 2.2:1 | 30 | Potato | Sprayed on foliage | Black Leg | 90 |

TABLE II-continued

| Analysis* | % Urea % Divalent Cation | Application Rate (gal/acre) | Crop Treated | Application Method | Disease Organism | Results (% control) |
|---|---|---|---|---|---|---|
| 18-0-0-7 Ca | 5.6:1 | 20 | Onion | Sprayed on foliage | Neck Rot | 80 |
| 15-0-3-4(Ca)-1.5(Mg.)-0.2(Zn)-0.1(Cu) | 6.8:1 | 2 every 14 days | Potato | Sprayed on foliage | Blight | 90 |
| 14-0-0-11(Ca) | 2.8:1 | 50–80 | Potato | Sub-surface root zone | Soft Rot | 80 |
| 18.0-0-0-7(Ca) | 5.6:1 | 6 | Radish and Cauliflower | Sub-surface root zone | Club Root | 75–80 |
| 9-0-0-9(Ca) or 18-0-0-7(Ca) | 2.2:1 or 5.6:1 | 20 | Potato | Sub-surface root zone | Rizocotina | 50–60 |
| | | 20 | Strawberry | Sprayed on foliage and sub-surface root zone | Botrytis | 70 |
| 18-0-0-7(Ca) | 5.6:1 | 10 | Wheat | Sprayed on seed head | Head Smut | 80 |

*% N - % P$_2$O$_5$ - % K$_2$O - % Metal Cation

The foregoing description of the invention has been directed in primary part to particular preferred embodiments in accordance with the requirements of the patent statutes and for purposes of explanation and illustration. It will be apparent, however, to those skilled in the art that many modifications and changes in the specifically described method may be made without departing from the true spirit and scope of the invention. In particular, it is not intended that the present invention be restricted to the particular crops and disease organisms illustrated, but that all crops and diseases responding to the described treatment should be included. Therefore, the invention is not restricted to the preferred embodiments described but covers all modifications which may fall within the scope of the following claims.

What is claimed is:

1. A method of inhibiting the growth of disease organisms on and in plants, comprising:
   directly applying to the seeds, stems, bark, leaves, seed heads or sub-surface rooting area soil an effective amount of an aqueous solution comprising about 1 to 40 percent-by-weight urea, a first water-soluble salt having a monovalent anion and a divalent alkaline earth cation selected from the group consisting of calcium, magnesium, and mixtures thereof, and a second water-solable salt having a monovalent anion and a divalent transition metal cation selected from the group consisting of zinc, manganese, copper, iron, cobalt, nickel and mixtures thereof;
   the weight percent ratio of urea to divalent cations from said water-soluble salts being from about 0.25–10.0 to 1.0, said aqueous solution having a pH between about 2.5 and 8.0 and being applied at a rate of about 2 to 100 gallons per acre, so that the concentration of at least one of said alkaline earth metal cations and at least one of said transition metal cations in the tissue of said plants is increased to a level that is about 2 to 4 times the normal level prior to being treated with said aqueous solution so that the growth of disease organisms on or in said plants is inhibited.

2. The method of claim 1 wherein said first salt is selected from the group consisting of calcium chloride, calcium nitrate, magnesium chloride, magnesium nitrate and mixtures thereof.

3. The method of claim 2 wherein said second salt is selected from the group consisting of zinc chloride, zinc nitrate, manganese chloride, manganese nitrate, copper chloride, copper nitrate and mixtures thereof.

4. The method of claim 1 wherein the concentration of at least one of the following divalent metal cations in the tissue of said plants is increased to be within the following ranges: calcium level in the tissue of said plants that is about 2 to 3 times the normal level prior to being treated with said aqueous solution, about 1000–4000 ppm magnesium, about 100–300 ppm manganese, about 60–160 ppm zinc, about 20–60 ppm copper, about 100–300 ppm iron, about 0.1–0.3 ppm cobalt or about 0.1–0.2 ppm nickel.

5. A method for inhibiting the growth of disease organisms on and in plants, comprising:
   preparing an aqueous solution comprising urea, a first water-soluble salt of a monovalent anion and a divalent alkaline earth cation selected from the group consisting of calcium, magnesium, and mixtures thereof, and a second water-soluble salt of a monovalent anion and a divalent transition metal cation selected from the group consisting of zinc, manganese, copper, iron, cobalt, nickel and mixtures thereof wherein the weight percent ratio of urea to divalent cations is from about 0.25–10.0 to 1.0; and
   directly applying to the seeds, stems, bark, leaves, seed heads or sub-surface root zones of said plants said aqueous solution at a rate and amount sufficient to increase the concentration of at least one of said alkaline earth metal cations and at least one of said transition metal cations in the tissue of said plants to a level that is about 2 to 4 times the normal level prior to being treated with said aqueous solution to inhibit the growth of disease organisms on or in said plants.

6. The method of claim 5 wherein said anion is selected from the group consisting of nitrate, chloride, bromide and mixtures thereof.

7. The method of claim 6 wherein said first salt is selected from the group consisting of calcium chloride, calcium nitrate, magnesium chloride, magnesium nitrate and mixtures thereof and said second salt is selected from the group consisting of zinc chloride, zinc nitrate, manganese chloride, manganese nitrate, copper chloride, copper nitrate and mixtures thereof.

8. The method of claim 7 wherein said first salt is calcium chloride and said second salt is copper chloride.

9. The method of claim 5 further comprising adjusting or maintaining the pH of said aqueous solution between about 2.5 and 8.0.

10. The method of claim 5 wherein said aqueous solution comprises from about 1 to 40 percent-by-weight urea and from about 1 to 60 percent-by-weight said water-soluble salts.

11. The method of claim 10 wherein said weight percent ratio of urea to divalent cations is from about 2.0–7.0 to 1.0.

12. The method of claim 5 wherein said aqueous solution is applied to said plants at a rate of about 2 to 100 gallons per acre.

13. The method of claim 5 wherein the concentration of at least one of the following dialent metal cations in the tissue of said plants is increased to be within the following ranges: calcium level in the tissue of said plants that is about 2 to 3 times the normal level prior to being treated with said aqueous solution, about 1000–4000 ppm magnesium, about 100–300 ppm manganese, about 60–160 ppm zinc, about 20–60 ppm copper, about 100–300 ppm iron, about 0.1–0.3 ppm cobalt or about 0.1–0.2 ppm nickel.

14. A method for inhibiting the growth of disease organisms on and in plants, comprising:

supplying an aqueous solution comprising urea, a first water-soluble salt of a monovalent anion and a divalent alkaline earth cation selected from the group consisting of calcium, mangnesium, and mixtures thereof, and a second water-soluble salt of a monovalent anion and a divalent transition metal cation selected from the group consisting of zinc, mangnesium, copper, iron, cobalt, nickel and mixtures thereof wherein the weight percent ratio of urea to divalent cations is from about 0.25–10.0 to 1.0 and the pH of said solution is between about 2.5 and 8.0; and directly applying to the seeds, stems, bark, leaves, seed heads or sub-surface root zones of said plants said aqueous solution at a rate and amount sufficient to increase the concentration of at least one of said alkaline earth metal cations and at least one of said transition metal cations in the tissue of said plants to a level that is about 2 to 4 times the normal level prior to being treated with said aqueous solution to inhibit the growth of disease organisms on or in said plants.

15. The method of claim 14 wherein said anion is selected from the group consisting of nitrate, chloride, bromide and mixtures thereof.

16. The method of claim 15 wherein said aqueous solution comprises from about 1 to 40 percent-by-weight urea and from about 1 to 60 percent-by-weight said water-soluble salts and said weight percent ratio of urea to divalent cations is from about 2.0–7.0 to 1.0.

* * * * *

UNITED STATES PATENT AND TRADEMARK OFFICE
CERTIFICATE OF CORRECTION

PATENT NO. : 6,086,923
DATED : July 11, 2000
INVENTOR(S) : Jerry H. Stoller

It is certified that error appears in the above-indentified patent and that said Letters Patent is hereby corrected as shown below:

Col. 9, line 11, replace "dialent" with --divalent--.

Col. 10, line 2, replace "mangnesium" with --manganese--.

Signed and Sealed this

Third Day of April, 2001

*Attest:*

NICHOLAS P. GODICI

*Attesting Officer*  *Acting Director of the United States Patent and Trademark Office*